United States Patent [19]
Takada et al.

[11] Patent Number: 5,965,602
[45] Date of Patent: Oct. 12, 1999

[54] PESTICIDAL COMPOSITION

[75] Inventors: Yoji Takada, Toyonaka; Izumi Fujimoto, Minoo, both of Japan

[73] Assignee: Sumitomo Chemical Company Ltd., Osaka, Japan

[21] Appl. No.: 08/739,569

[22] Filed: Oct. 30, 1996

[30] Foreign Application Priority Data

Oct. 31, 1995 [JP] Japan ................................. 7-283315
Aug. 8, 1996 [JP] Japan ................................. 8-210094

[51] Int. Cl.$^6$ .......................... A01N 43/36; A01N 53/00
[52] U.S. Cl. ................................. 514/427; 514/531
[58] Field of Search ........................ 514/427, 531

[56] References Cited

U.S. PATENT DOCUMENTS 5,010,098  4/1991  Brown et al. ........................ 514/426

FOREIGN PATENT DOCUMENTS 0 492 171 A1  7/1992  European Pat. Off. .

OTHER PUBLICATIONS

Bartels, D.W. et al, [*Insecticidal and Microbial Control of Lepidopteran Lervae in Minnesota Cabbage*], Arthropod Management Tests, vol. 19., pp. 64–65 (1994).

Tomlin, C., "The Pesticide Manual", 10th Edition (1995) pp. 783–785.

Database WPI, Section Ch, Week 9101, Derwent Publications Ltd., London, GB, Class C03, AN 91–003110, Nov. 15, 1990.

Chemical Abstracts, vol. 103, No. 19, Nov. 11, 1985; AN 155778.

Whitehead et al., [*Performance of Pirate, Insecticide–Miticide, Against Cotton Pests in the Mid–South in 1992*], Proceedings: Beltwide Cotton Conference, vol. 2, pp. 832–834 (1993).

Micinski et al., [*Efficacy of Selected Insecticide Mixtures for Control of the Bollworm/Tobacco Budwork Complex*], Arthropod Management Tests, vol. 20, pp. 207–208 (1995).

Sears et al., [*Effects of Various Rates and Combinations of Insecticides and Adjuvants on the Control of Colorado Potato Beetle*], Pest Management Research Report—Insects and Diseases, pp. 117–118 (1994).

Lund et al., [*Control of Colorado Potato Bettle on Patatoes with Pyrrole and Cypermethrin*], Pest Management Research Report—Insects and Diseases, pp. 92–93 (1994).

Pitplado, R.E., [*Insect Control in Cabbage*], Pest Management Research Report—Insects and Disease, (1992) pp. 1–3.

*Primary Examiner*—Allen J. Robinson
*Attorney, Agent, or Firm*—Pillsbury Madison & Sutro LLP

[57] ABSTRACT

The present invention provides a pesticidal composition which comprises 4-bromo-2-(4-chlorophenyl)-1-ethoxymethyl-5-trifluromethylpyrrole-3-carbonitrile and at least one pyrethroidal compound as active ingredients, and an inert carrier, and an insecticidal/acaricidal method applying 4-bromo-2-(4-chlorophenyl)-1-ethoxymethyl-5-trifluoromethylpyrrole-3-carbonitrile and at least one pyrethroidal compound to noxious insects, acarina, or the locus where noxious insects or acarina inhabit.

10 Claims, No Drawings

PESTICIDAL COMPOSITION

DETAILED DESCRIPTION OF THE INVENTION

1. Field of Art in Which the Invention Belongs

The present invention relates to a pesticidal composition which is effective in particular against vector or nuisance pests such as cockroaches and house dust mites and wood pests such as termites, and a method for controlling such noxious insects and/or acarina.

Various kinds of pesticidal agents have been developed in the past, but it has been hard to control cockroaches, which are said a prototype of vector or nuisance pests, and no effective means for control of the cockroaches has yet been made available.

Also, in view of increase damages by house dust mites in recent years, development of a pesticidal composition capable of controlling both of cockroaches and house dust mites has been desired.

The present invention provides a pesticidal composition which comprises 4-bromo-2-(4-chlorophenyl)-1-ethoxymethyl-5-trifluoromethylpyrrole-3-carbonitrile and at least one pyrethroidal compound as active ingredients (this composition being hereinafter referred to as the composition of the present invention), and a method for controlling noxious insects and/or acarina which comprises applying an effective amount of 4-bromo-2-(4-chlorophenyl)-1-ethoxymethyl-5-trifluoromethylpyrrole-3-carbonitrile and at least one pyrethroidal compound to the noxious insects and/or acarina, or the locus where the noxious insects and/or acarina inhabit. Said composition and method are very effective for controlling vector or nuisance pests, particularly cockroaches and house dust mites.

The composition and the method of the present invention are also highly effective for control of wood pests such as termites.

4-Bromo-2-(4-chlorophenyl)-1-ethoxymethyl-5-trifluoromethylpyrrole-3-carbonitrile is a compound disclosed in The Pesticide Manual, 10th ed., pp. 7–8, published by The British Crop Protection Council, and can be produced according to the processes described in U.S. Pat. No. 4,857,651, etc.

The pyrethroidal compounds which may be used in the present invention include, for example, phenothrin, cyphenothrin, permethrin, cypermethrin, deltamethrin, cyhalothrin, cyfluthrin, acrinathrin, furamethrin, resmethrin, prallethrin, allethrin, fenvalerate, ethofenprox, silafluofen, fluvalinate, flucythrinate, tetramethrin, imiprothrin, transfluthrin, empenthrin, bifenthrin, and 3-(4-ethoxyphenyl)-3-methyl-6-(4-fluoro-3-phenoxyphenyl)hex-1-yne.

The weight ratio of 4-bromo-2-(4-chlorophenyl)-1-ethoxymethyl-5-trifluoromethylpyrrole-3-carbonitrile to the pyrethroidal compound(s) in the composition of the present invention is usually within the range of 99:1 to 5:95, preferably 99:1 to 10:90.

Especially when the pyrethroidal compound is phenothrin, cyphenothrin, permethrin, cypermethrin, ethofenprox or silafluofen, the weight ratio of 4-bromo-2-(4-chlorophenyl)-1-ethoxymethyl-5-trifluoromethylpyrrole-3-carbonitrile to the pyrethroidal compound is preferably within the range of 90:10 to 10:90, more preferably 90:10 to 50:50, as the combination of said ingredients with their weight ratio in the above-defined range is capable of more efficient control of vector or nuisance and wood pests owing to the excellent synergistic effect of the two ingredients.

While the composition of the present invention has the excellent pesticidal activities against various species of pests, it shows particularly high efficacy for control of vector or nuisance pests including cockroaches such as German cockroach [*Blattella germanica*], smokybrown cockroach [*Periplaneta fuliginosa*], American cockroach [*Periplaneta americana*], brown cockroach [*Periplaneta brunnea*] and oriental cockroach [*Blatta orientalis*], house mites such as mold mite [*Tyrophagus putrescentiae*], American house dust mite [*Dermatophagoides farinae*] and Cheyletid mites [Chelacaropsis], fleas such as cat flea [*Ctenocephalides felis*], mosquitos such as brown house mosquito [*Culex pipiens pallens*] and Asian tiger mosquito [*Aedes albopictus*], and flies such as housefly [*Musca domestica*], and wood pest including termites such as Formosan substerranean termite [*Copptotermes formosanus*], Japanese subterranean termite [*Reticulitermes speratus*], American common dry-wood termite [*Incistermes minor*], Daikoku dry-wood termite [*Cryptotermes domesticus*], Odontotermes formosanus, Coptotermes formosanus, Reticulitermes speratus, R. flavipes, R. hesperus, R. virginicus, R. tibialis, Incisitermes minor, Cryptotermes domesticus, Odontotermes formosanus, and Heterotermes aureus, termite species of the families (and pest genera) Mastotermitidae (Mastotermes species), Hodotermididae (Anacanthotermes, Zootermopsis species), Rhinotermitidae (Coptotermes, Heterotermes, Reticulitermes, Psammotermes, Prorhinotermes, Schedorhinotermes species), Kalotermitidae (Glyptotermes, Neotermes, Crvptotermes, Incisitermes, Kalotermes, Marginitermes species), Serritermitidae, and Termitidae (Pericapritermes, Allodontermes, Microtermes, Odontotermes, Nasutitermes, Termes, Amitermes, Globitermes, Microcerotermes species), Termopsidae (Hodotermopsis, Zootermopsis species), and other pest species of termites, raw logvermin such as bark beetles [Scolytidae], longicorn beetles [Cerambycidae], weevils [Curculionidae], pinhole borers [Platypodidae] and horntails [Siricidae], and dry wood vermin such as powderpost beetle [*Lyctus brunneus*], false powderpost beetles [*Bostrychidae*], deathwatch and drugstore beetles [Anobiidae] and drywooden longicorn bettle [*Stromatium longicorne*].

The composition of the present invention is also useful for control of agricultural pests such as diamondback moth [*Plutella xylostella*], common cabbageworm [*Pieris rapae crucivora*], tobaccocutworm [*Spodoptera litura*], melon thrips [*Thrips palmi*], tea green leafhopper [*Empoasca onukii*], appleleafminer [*Phyllonorycter ringoniella*], rice water weevil [*Lissorhoptrus oryzophilus*], Japanese beetle [*Popillia japonica*], striped flea beetle [*Phyllotreta*], Kanzawa spidermite [*Tetranychus kanzawai*] and broad mite [*Polyphaaotarsonemus latus*].

The composition of the present invention can be obtained usually by mixing the active ingredient compounds with a solid or liquid carrier and if necessary further adding a surfactant and other adjuvants necessary for formulating the desired preparations. The active ingredient compounds or a liquid containing them may be impregnated, for instance, in the base of a mosquito coil or mosquito mat. The composition of the present invention thus obtained may be in various formulation types, for example, oil solution, emulsifiable concentrate, wettable powder, and flowables such as suspension-in-water and emulsion-in-water, granules, dusts, aerosols, fumigants such as electric mosquito mat or liquid, smoking preparations such as mosquito coil, self-burning type smoking preparations, chemical reaction type smoking preparations and electrically heated type smoking preparations, fuming preparations such as fogging, and ULV preparations.

In these formulation, the active ingredient compounds are contained in a total amount of usually 0.001 to 95% by weight.

The solid carriers usable in these formulations include fine powders or granules of clays (kaolin clay, diatomaceous earth, bentonite, fubasami clay, acid clay, etc.), synthetic hydrous silicon oxide, talcs, ceramics, other inorganic minerals (sericite, quartz, sulfur, active carbon, calcium carbonate, etc.), and chemical fertilizers (ammonium sulfate, ammonium phosphate, ammonium nitrate, urea, ammonium chloride, etc.). The liquid carriers include water, alcohols (methanol, ethanol, etc.), ketones (acetone, methyl ethyl ketone, cyclohexanone, etc.), aromatic hydrocarbons (toluene, xylene, ethylbenzene, methylnaphthalene, etc.), non-aromatichydrocarbons (hexane, cyclohexane, kerosine, light oil, etc.),esters (ethyl acetate, butyl acetate, etc.), nitrites (acetonitrile, isobutyronitrile, etc.), ethers (diisopropyl ether, dioxane, etc.), acid amides (N,N-dimethylformamide, N,N-dimethylacetamide, etc.), halogenated hydrocarbons (dichloromethane, trichloroethane, carbon tetrachloride, etc.), dimethyl sulfoxide, and vegetable oils (soybean oil, cottonseed oil, etc.).

If necessary, an aerosol propellant such as butane gas, liquefied petroleum gas, dimethyl ether, carbon dioxide gas or the like may be added to the composition.

The surfactants usable in the present invention include, for example, alkylsulfuric esters, alkyl sulfonates, alkylarylsulfonates, alkylaryl ethers and their polyoxyethylenated products, polyethylene glycol ethers, polyhydric alcohol esters, and sugar-alcohol derivatives.

The formulation adjuvants such as adhesive agents and dispersants include casein, gelatin, sugars (starch, gum arabic, cellulose derivatives, alginic acid, etc.), lignin derivatives, bentonite, and synthetic water-soluble polymers (polyvinyl alcohol, polyvinyl pyrrolidone, polyacrylic acids, etc.). Stabilizers such as PAP (acidic isopropyl phosphate), BHT (2,6-di-tert-butyl-4-methylphenol), BHA (2-tert-butyl-4-methoxyphenol and 3-tert-butyl-4-methoxyphenol), vegetable oils, mineral oils, fatty acids, fatty acid esters and the like may be used as adjuvant.

As the base material of the mosquito coil, there can be used, for example, a mixture of vegetable powder such as woodmeal, pyrethrum marc, etc., and a binder such as Tabu powder, starch, glutein, etc.

As the base of the electric mosquito mat, there may be used, for example, a plate made by compacting the fibrils of cotton linter or a mixture of cotton linter and pulp.

As the base of the self-combustion type smoking preparations, mixtures of combustible substances such as nitrates, nitrites, guanizine salts, potassium chlorate, nitrocellulose, ethyl cellulose and woodmeal, pyrolysis stimulants such as alkali metal salts, bichromates and chromates, oxygen suppliers such as potassium nitrate, combustion aids such as melamine and wheat starch, extenders such as diatomaceous earth, binders such as synthetic pastes may be used.

As the base of the chemical reaction type fumigants, mixtures of heat generating substances such as sulfides, polysulfides and hydrosulfides of alkali metals, hydrous salts and calcium oxide, catalysts such as carbonaceous materials, iron carbide and activated clay, organic foaming agents such as azodicarbonamide, benzenesulfonylhydrazide, dinitropentamethylenetetramine, polystyrene and polyurethane, and fillers such as natural fiber can be used.

The flowables such as suspension-in-water and emulsion-in-water may be obtained generally by finely dispersing 1–75% by weight of active ingredient compounds in water containing 0.5–15% by weight of a suspension assistant (such as protective colloid or a substance capable of affording thixotropy) and 0–10% by weight of adjuvants (such as defoaming agent, anti-corrosive, stabilizer, spreading agent, infiltration assistant, antifreezing agent and mildewproofing agent).

A suspension-in-oil may be obtained likewise by using, instead of water, an oil in which the active ingredient compounds are scarcely soluble.

As protective colloid, gelatin, casein, gums, cellulose ethers, polyvinyl alcohol or the like can be used, and as the substance capable of affording thixotropy, bentonite, aluminum magnesium silicate, xanthane gum, polyacrylic acid or the like may be used.

The composition of the present invention obtained in the manner described above is usually applied in the form as it is when the composition is used as an oil solution, aerosol, fumigant, smoking preparation, fuming preparation, ULV preparation or the like. For use of an emulsifiable concentrate, wettable powder, flowable preparation or the like, the composition is usually applied after diluted with water. Generally dilution is made such that the concentration of the active ingredient compounds in the preparation will fall within the range of about 1–10,000 ppm.

The amount of the composition of the present invention to be applied is variable depending on the species of the pests to be controlled, the type of the formulation, the locus of application, method of application and other factors, but usually the effective amount of the active ingredient compounds is about 0.0001–10 g/m$^2$. Typically, for control of cockroaches, it is effective to spray an oil solution or an aerosol of the composition of the present invention at a rate of about 0.001–1 g per 1 m$^2$ in terms of the amount of the active ingredient compounds. In the case of a heat fumigant or smoking preparation, it is recommended to apply the preparation in the form of fume or smoke at a rate of about 0.0001–1 g per 1 m$^3$ in terms of the amount of the active ingredient compounds. For control of termites, the composition of the present invention formulated into an oil solution, emulsifiable concentrate, flowable, microcapsules or the like is sprayed or spread on and/or in the soil or the wood surface at a rate of about 0.01–100 g per 1 m$^2$ in terms of the amount of the active ingredient compounds.

In the method for controlling noxious pests and/or acarina according to the present invention, it is convenient to use the composition of the present invention which is a mixture of 4-bromo-2-(4-chlorophenyl)-1-ethoxymethyl-5-trifluoromethylpyrrole-3-carbonitrile and at least one pyrethroidal compound, but it is possible to use the respective active ingredient compounds or the formulations thereof independently or in combination in the suitable ways. In the latter case, the ratio of the active ingredient compounds applied is the same as the above-defined weight ratio of the active ingredients in the composition of the present invention, and the amounts of the compounds applied are the same as the above-defined amounts of the active ingredient compounds of the composition of the present invention.

EXAMPLES

The present invention will be described more specifically according to the formulation examples and test examples, but the embodiments of the present invention are not limited to these examples.

Formulation Example 1

0.5 Part by weight of d-Phenothrin [3-phenoxybenzyl (1R)-cis,trans-chrysanthemate], 0.1 part by weight of 4-bromo-2-(4-chlorophenyl)-1-ethoxymethyl-5-trifluoromethylpyrrole-3-carbonitrile, 49.7 parts by weight of Isopar M (an aliphatichydrocarbon available from Exxon Chemical Co., Ltd.) and 49.7 parts by weight of Chlorothen Nu (a chlorinated hydrocarbon available from Dow Chemical Co., Ltd.) are mixed to obtain an oil solution.

Formulation Example 2

One part by weight of d-Phenothrin, 0.1 part by weight of 4-bromo-2-(4-chlorophenyl)-1-ethoxymethyl-5-trifluoromethylpyrrole-3-carbonitrile, 49.45 parts by weight of Isopar M (mentioned above) and 49.45 parts by weight of Chlorothen Nu (mentioned above) are mixed to obtain an oil solution.

Formulation Example 3

0.5 Part by weight of Cyphenothrin [α-cyano-3-phenoxybenzyl(1R)-cis,trans-chrysanthemate], 0.1 part by weight of 4-bromo-2-(4-chlorophenyl)-1-ethoxymethyl-5-trifluoromethylpyrrole-3-carbonitrile and 99.4 parts by weight of kerosene are mixed to obtain an oil solution.

Formulation Example 4

One part by weight of d-Phenothrin, 0.1 part by weight of 4-bromo-2-(4-chlorophenyl)-1-ethoxymethyl-5-trifluoromethylpyrrole-3-carbonitrile and 98.9 parts by weight of diesel oil are mixed to obtain an oil solution.

Formulation Example 5

The procedure of Formulation Example 3 is followed except for use of Permethrin [3-phenoxybenzyl 2,2-dimethyl-3-(2,2-dichlorovinyl)cyclopropane-carboxylate] in place of Cyphenothrin to obtain an oil solution.

Formulation Example 6

The procedure of Formulation Example 3 is followed except for use of Cypermethrin [α-cyano-3-phenoxybenzyl 2,2-dimethyl-3-(2,2-dichlorovinyl)cyclopropanecarboxylate] in place of Cyphenothrin to obtain an oil solution.

Formulation Example 7

One part by weight of Tetramethrin, 5 parts by weight of 4-bromo-2-(4-chlorophenyl)-1-ethoxymethyl-5-trifluoromethylpyrrole-3-carbonitrile, 84.6 parts by weight of Isopar M (mentioned above) and 9.4 parts by weight of Chlorothen Nu (mentioned above) are mixed to obtain an oil solution.

Formulation Example 8

3 Parts by weight of Imiprothrin, 5 parts by weight of 4-bromo-2-(4-chlorophenyl)-1-ethoxymethyl-5-trifluoromethylpyrrole-3-carbonitrile, 20 parts by weight of isopropyl myristate, 10 parts by weight of Reodol SP-L10 (sorbitan monolaurate produced by Kao Corp.) and 62 parts by weight of Neothiozol (solvent produced by Chuo Kasei Co., Ltd.) are mixed. 10 Parts by weight of the obtained mixture and 50 parts by weight of deionized water are put into an aerosol container and, after attaching a valve to the container, 40 parts by weight of liquefied petroleum gas is charged thereinto under pressure through the valve to obtain an aqueous aerosol.

Formulation Example 9

A mixture consisting of 0.1 part by weight of Imiprothrin, 0.3 part by weight of 4-bromo-2-(4-chlorophenyl)-1-ethoxymethyl-5-trifluoromethylpyrrole-3-carbonitrile, 19.6 parts by weight of soft alkylbenzene (a solvent available from Mitsubishi Chemical Co., Ltd.) and 40 parts by weight of Isopar M (mentioned above) is contained in an aerosol container and, after attaching a valve to the container, 40 parts by weight of liquefied petroleum gas is charged thereinto under pressure through the valve to obtain an oily aerosol.

Formulation Example 10

5 Parts by weight of Permethrin, 5 parts by weight of 4-bromo-2-(4-chlorophenyl)-1-ethoxymethyl-5-trifluoromethylpyrrole-3-carbonitrile, 10 parts by weight of Newcalgen KH-13 (a surfactant available from Takemoto Yushi KK) and 80 parts by weight of Solvesso 150 (an aromatic solvent available from Exxon Chemical Co., Ltd.) are mixed to obtain an emulsifiable concentrate.

Test Example 1

A pair of trigonal shelters (each comprising a trigonal prismatic structure made by combining three pieces of 15 cm×3.5 cm veneer board), each containing 5 imaginal female German cockroaches, were set catercornered on the floor of a 28 $m^3$ room. A ceramic (4 cm×4 cm×1.2 cm) coated with an acetone solution of (S)-α-cyano-3-phenoxybenzyl (1R)-cis,transchrysanthemate [Cyphenothrin, an ester whose alcohol portion is (S)-form, hereinafter referred to as compound (I)) and a ceramic (4 cm×4 cm×1.2 cm) coated with an acetone solution of 4-bromo-2-(4-chlorphenyl)-1-ethoxymethyl-5-trifluoromethylpyrrole-3-carbonitrile (hereinafter referred to as compound (II)) were placed respectively at the center of the room, and the ceramic coated with an acetone solution of the compound (I) was heated at 250° C. while the ceramic coated with an actone solution of the compound (II) was heated at 300° C., both by an electric heater for 60 minutes to fumigate the compound (I) and the compound (II) respectively. 120 Minutes after the start of heating, the test insects were transferred to the separate containers and their mortality 7 days after the test was examined. The results are shown in Table 1.

TABLE 1

| Specimen | Dose (mg/$m^3$) | Mortality (%) |
| --- | --- | --- |
| Compound (I) | 3.13 | 11 |
| Compound (II) | 25 | 20 |
| Compound (I) + Compound (II) | 3.13 + 25 | 89 |

Test Example 2

A pair of trigonal shelters (each comprising a trigonal prismatic structure made by combining 3 sheets of 15 cm×5 cm veneer board), each containing 3 imaginal male Americal cockroaches, were set catercornered on the floor of a 28 $m^3$ room. A ceramic (4 cm×4 cm×1.2 cm) coated with an acetone solution of the compound (I) and a ceramic (4 cm×4 cm×1.2 cm) coated with an acetone solution of the compound (II) were placed respectively at the center of the room, and the ceramic coated with an acetone solution of the compound (I) was heated at 250° C. while the ceramic coated with an acetone solution of the compound (II) was heated at 300° C., both by an electric heater for 60 minutes to fumigate the compound (I) and the compound (II) respectively. 120 Minutes after the start of heating, the test insects were transferred to the separate containers and their mortality one day after the test was examined. The results are shown in Table 2.

A similar test was conducted using 6 male smokybrown cockroaches to obtain the results shown in Table 3.

TABLE 2

| Specimen | Dose (mg/m$^3$) | Mortality (%) |
| --- | --- | --- |
| Compound (I) | 3.13 | 0 |
| Compound (II) | 25 | 0 |
| Compound (I) + Compound (II) | 3.13 + 25 | 100 |

TABLE 3

| Specimen | Dose (mg/m$^3$) | Mortality (%) |
| --- | --- | --- |
| Compound (I) | 3.13 | 0 |
| Compound (II) | 25 | 0 |
| Compound (I) + Compound (II) | 3.13 + 25 | 75 |

Test Example 3

A 4 cm-diameter filter paper was placed on an aluminum tray and, with a tacky substance (Corponil available from Nippon Synthetic Chemical Co., Ltd.) applied along the edges of the filter paper to prevent runaway of the test mites, 50–100 mold mites were released on the filter paper with feed placed thereon.

The thus prepared aluminum tray with the mold mites released thereon was set at a corner of the floor of a 28 m$^3$ room. Then a ceramic (4 cm×4 cm×1.2 cm) coated with an acetone solution of the compound (I) and a ceramic (4 cm×4 cm×1.2 cm) coated with an acetone solution of the compound (II) were placed respectively at the center of the room, and the ceramic coated with an acetone solution of the compound (I) was heated at 250° C. while the ceramic coated with an acetone solution of the compound (II) was heated at 300° C., both by an electric heater for 60 minutes to fumigate the compound (I) and the compound (II) respectively. 120 Minutes after the start of heating, the aluminum tray with the mites placed thereon was taken out and the mortality of the mites one day after the test was examined. The results are shown in Table 4.

A similar test was conducted using American house dust mites in place of mold mites to obtain the results shown in Table 5.

TABLE 4

| Specimen | Dose (mg/m$^3$) | Mortality (%) |
| --- | --- | --- |
| Compound (I) + Compound (II) | 3.13 + 25 | 100 |

TABLE 5

| Specimen | Dose (mg/m$^3$) | Mortality (%) |
| --- | --- | --- |
| Compound (I) + Compound (II) | 3.13 + 25 | 84 |

Test Example 4

A 4 cm-diameter filter paper was placed on an aluminum tray and, with a tacky substance (Corponil available from Nippon Synthetic Chemical Co., Ltd.) applied along the edges of the filter paper to prevent runaway of the test mites, 20 cheyletid mites [*Chelacaropsis moorei* Baker] were released on the filter paper.

The thus prepared aluminum tray with the test mites released thereon was set at a corner of the floor of a 28 m$^3$ room. Then a ceramic (4 cm×4 cm×1.2 cm) coated with an acetone solution of the compound (I) and a ceramic (4 cm×4 cm×1.2 cm) coated with an acetone solution of the compound (II) were placed respectively at the center of the room, and the ceramic coated with an acetone solution of the compound (I) was heated at 250° C. while the ceramic coated with an acetone solution of the compound (II) was heated at 300° C., both by an electric heater for 60 minutes to fumigate the compound (I) and the compound (II) respectively. 120 Minutes after the start of heating, the aluminum tray with the test mites placed thereon was taken out and the mortality of the mites 5 days after the test was examined. The results are shown in Table 6.

TABLE 6

| Specimen | Dose (mg/m$^3$) | Mortality (%) |
| --- | --- | --- |
| Compound (I) + Compound (II) | 3.13 + 25 | 100 |

Test Example 5

The 3-litre glass beakers each containing 60–80 imaginal cat fleas were set at the three corners of the floor of a 28 m$^3$ room. Then a ceramic (4 cm×4 cm×1.2 cm) coated with an acetone solution of the compound (I) and a ceramic (4 cm×4 cm×1.2 cm) coated with an acetone solution of the compound (II) were placed respectively at the center of the room, and the ceramic coated with an acetone solution of the compound (I) was heated at 250° C. while the ceramic coated with an acetone solution of the compound (II) was heated at 300° C., both by an electric heater for 60 minutes to fumigate the compound (I) and the compound (II) respectively. 120 Minutes after the start of heating, the test insects were transferred to the separate containers and their mortality one day after the test was examined. The results are shown in Table 7.

TABLE 7

| Specimen | Dose (mg/m$^3$) | Mortality (%) |
| --- | --- | --- |
| Compound (I) + Compound (II) | 3.13 + 25 | 100 |

Test Example 6

A 15 cm long and 1.7 cm-inner diameter glass tube was packed centrally thereof with soil along a length of 3 cm, and the chemical solutions shown in Table 8 were applied to the surface on one side of the soil mass. Then 4% agar was placed on both sides of the soil mass and the Formosan subterranean termites (50 workers and 5 soldiers) were released in the space of the glass tube on the side where no chemical solution was applied. One week thereafter, the situation of the soil mass excavated by the termites was observed. The same test was repeated thrice. The results are shown in Table 8.

In the column of "Results" in Table 8, "All" indicates that the termites have made their way through the whole mass of soil and further passed through the agar layer on the opposite side, "B" indicates that they have passed through the soil mass and reached halfway of the agar layer on the opposite side, and "C" indicates that they have failed to get through the chemical-applied side of the soil mass.

TABLE 8

| Specimen | Concentration (ppm) | Result |
| --- | --- | --- |
| Compound (II) 10FL + Ethofenprox 20EC | 500 + 500 | CCC |
| Compound (II) 10FL + Cypermethrin 6EC | 500 + 500 | CCC |
| Compound (II) 10FL + Permethrin 50EC | 500 + 100 | CCC |
| Compound (II) 10FL | 500 | AAA |
| Ethofenprox 20EC | 500 | AAC |
| Cypermethrin 6EC | 500 | AAC |
| Permethrin 50EC | 100 | AAA |
| No treatment | — | AAA |

Compound (II) 10FL: a 10% flowable preparation of the compound (II) (Kotetsu 10FL available from Kumiai Chemical Co., Ltd.)
Ethofenprox 20EC: a 20% emulsiable concentrate of Ethofenprox (Trebon Emulsion available from Kumiai Chemical Co., Ltd.)
Cypermethrin 6EC: a 6% emulsiable concentrate of Cypermethrin (Agrothrin Emulsion available from Kumiai Chemical Co., Ltd.)
Permethrin 50EC: a 50% emulsiable concentrate of Permethrin [a permethrin emulsion composed of 50% of Permethrin, 45% of xylene and 5% of Sorpol SM-200 (polyoxyethylene castor oil, a surfactant available from Toho Chemical Co., Ltd.)

Test Example 7

A trigonal shelter (comprising a trigonal prismatic structure made by combining three sheets of 15 cm×5 cm veneer board) containing 3 female and 3 male imaginal smoky-brown cockroaches was placed at the center of a 0.34 m³ glass chamber. Then 4 ml of each of the oil solutions of the concentrations shown in Table 9, prepared according to Formulation Example 7, was sprayed into the glass chamber. After passage of 10 minutes from spraying, the glass chamber was ventilated for 5 minutes, then the cockroaches were transferred to the separate container and their mortality 3 days after spraying was examined. The results are shown in Table 9.

TABLE 9

| Specimen | Concentration (%) | Mortality (%) |
| --- | --- | --- |
| Tetramethrin | 1 | 0 |
| Compound (II) | 5 | 17 |
| Tetramethrin + compound (II) | 1 + 5 | 100 |

The pesticidal composition and the insecticidal/acaricidal method according to the present invention are effective for controlling pests, especially vector or nuisance pests such as cockroaches and house dust mites and wood pest such as termites.

What is claimed is:

1. A pesticidal composition which comprises synergistic effective ammounts of 4-bromo-2-(4-chlorophenyl)-1-ethoxymethyl-5-trifluoro-methylpyrrole-3-carbonitrile and permethrin as active ingredients, and an inert carrier.

2. The pesticidal composition according to claim 1, wherein the weight ratio of 4-bromo-2-(4-chlorophenyl)-1-ethoxymethyl-5-trifluoromethylpyrrole-3-carbonitrile and permethrin is within the range of 90:10 to 50:50.

3. The pesticidal composition according to claim 1, wherein the weight ratio of 4-bromo-2-(4-chlorophenyl)-1-ethoxymethyl-5-trifluoromethylpyrrole-3-carbonitrile and permethrin is within the range of 99:1 to 50:50.

4. A method for controlling noxious insects or acarina which comprises applying synergistic effective amounts of 4-bromo-2-(4-chlorophenyl)-1-ethoxymethyl-5-trifluoromethylpyrrole-3-carbonitrile and permethrin to the noxious insects or acarina or a locus where noxious insects or acarina inhabit.

5. The method according to claim 4, wherein the insects comprise cockroaches.

6. The method according to claim 4, wherein the insects comprise termites.

7. The method according to claim 4, wherein the acarina comprise house dust mites.

8. The method according to claim 4, wherein the weight, ratio of 4-bromo-2-(4-chlorophenyl)-1-ethoxymethyl-5-trifluoromethylpyrrole-3-carbonitrile and permethrin is within the range of 90:10 to 50:50.

9. The method according to claim 8, wherein the insects comprise termites.

10. The method according to claim 4, wherein the weight, ratio of 4-bromo-2-(4-chlorophenyl)-1-ethoxymethyl-5-trifluoromethylpyrrole-3-carbonitrile and permethrin is within the range of 99:1 to 50:50.

* * * * *